United States Patent [19]

Yquel et al.

[11] Patent Number: 4,738,537
[45] Date of Patent: Apr. 19, 1988

[54] METHOD AND APPARATUS FOR MEASURING A QUANTITY OF A GREASY PRODUCT ON A SURFACE TO BE INVESTIGATED, AND A TAKE UPSTRIP FOR THE GREASY PRODUCT

[75] Inventors: Jean-Pierre Yquel, Colombes; Jean-Francois Grollier, Paris; Paul Krien, Verrieres Le Buisson, all of France

[73] Assignee: L'Oreal, Paris, France

[21] Appl. No.: 856,984

[22] Filed: Apr. 29, 1986

[30] Foreign Application Priority Data

Apr. 29, 1985 [FR] France ................................ 85 06481

[51] Int. Cl.$^4$ ...................... G01N 21/55; G01N 1/28; A61B 10/00
[52] U.S. Cl. ..................................................... 356/445
[58] Field of Search ............ 356/36, 38, 326, 445–448, 356/382–385, 244, 248, 252, 254

[56] References Cited

U.S. PATENT DOCUMENTS

| | | | |
|---|---|---|---|
| 4,030,837 | 6/1977 | Kojima et al. | 356/209 |
| 4,313,393 | 2/1982 | Barbuscio et al. | 116/200 |
| 4,480,921 | 11/1984 | Leveque et al. | 356/434 |

FOREIGN PATENT DOCUMENTS

| | | |
|---|---|---|
| 2353224 | 7/1975 | Fed. Rep. of Germany . |
| 2404845 | 9/1977 | France .......................... 356/434 |
| 2480461 | 10/1981 | France . |

OTHER PUBLICATIONS

Patents Abstracts of Japan, vol. 6, No. 175 (P-141) [1053], Sep. 1982, & JP-A-57 90 161 (Rikoo Tokei K.K.).

Primary Examiner—R. A. Rosenberger
Assistant Examiner—S. McGowan
Attorney, Agent, or Firm—Cushman, Darby & Cushman

[57] ABSTRACT

A take-up strip is applied to the element to be investigated, (for example the skin or the hair of a living subject), for a given time and with a given pressure; the side of this strip intended to come into contact with the element to be investigated is matt; the quantity of light reflected by the matt side of the strip is measured before and after impregnation with the greasy product: the quantity of the greasy product located on the surface of the element investigated is derived from the reflection measurement. The detection means is constituted by a phototransistor whose output signal is processed by an analog/digital converter associated with a programmable computer; the strip is disposed on a displaceable support. The reflection reading all along the strip gives a brightness curve in accordance with the location on the strip. For the hair, this curve reflects the greasy aspect from the root to its tip.

13 Claims, 2 Drawing Sheets

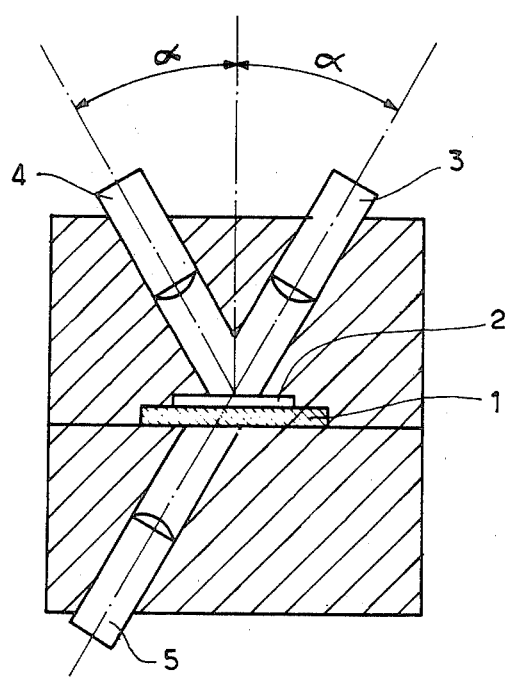
FIG. 1
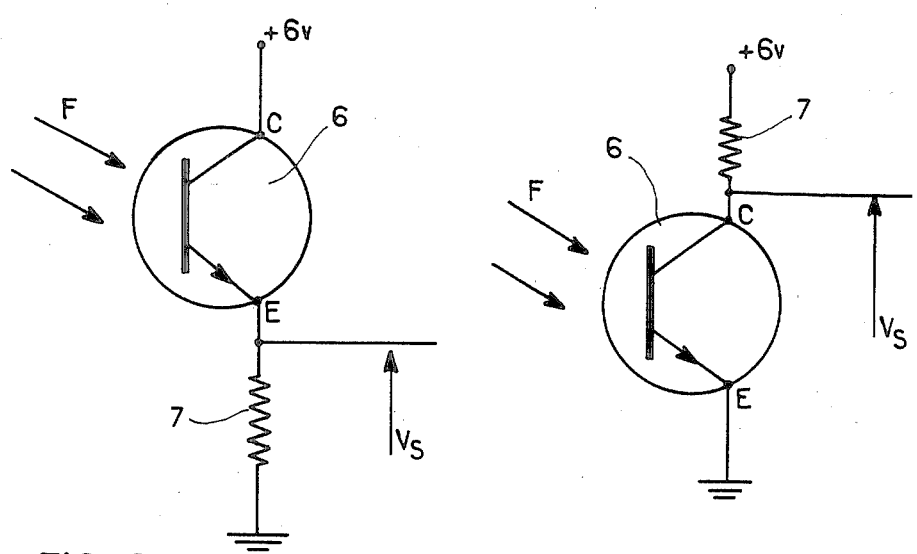
FIG. 2
FIG. 3

METHOD AND APPARATUS FOR MEASURING A QUANTITY OF A GREASY PRODUCT ON A SURFACE TO BE INVESTIGATED, AND A TAKE UPSTRIP FOR THE GREASY PRODUCT

FIELD OF THE INVENTION

The present invention relates to a method and apparatus for detecting a quantity of a greasy product on the surface of an element to be investigated, in particular on the skin, body hair or hair of the scalp, in vivo. This greasy product can be sebum secreted by the skin or the hair, or an oil based substance remaining on a skin which has only absorbed a portion thereof after a certain time after application of the said oily product. The invention also relates to the take-up device for the greasy product on the subject in vivo.

PRIOR ART

In the preamble of German Patent Application No. 3 213 944, a certain number of methods are listed for evaluating the extent of the greasy film which is present on the skin surface. This patent application itself relates to a method for evaluating the greasy film of the skin surface, in which a side of a support coated with a finely distributed adsorbent, preferably a mineral one, is placed into contact with the surface of the skin, the greasy substances are rendered visible by analysis or by the action of reagents, and the colour change is evaluated photographically or photometrically.

From the "CA SELECTS-COSMETIC CHEMICAL, ISSUE 19, 1984, 101: 68596 h", a method is also known for the measurement of sebum secretions using a multilayer support applied to the skin for taking up the sebum. This multilayer support comprises a cellular polyethylene layer, a paper layer, a layer of black colour containing ethyl acrylate, and a layer of a white colour of a thickness of 5 $\mu$m containing ethyl acrylate. When this multilayer support is applied to the skin, the black colour appearing on the layer of the white colour depends on the quantity of sebum secreted.

Amongst all the known methods, those based on the choice of a translucent plate as the take-up element for the sebum on the skin and the measurement of the quantity of light transmitted through this support, will be considered. It is known that a good correlation exists between the trasparency of a ground glass strip previously applied to the skin zone to be investigated during a given time and with a given pressure on the one hand, and on the other hand, the quantity of the greasy product deposited on the said strip.

In particular, the French Pat. No. 2480461 describes an apparatus intended for the determination of the quantity of the greasy product located on the skin surface. In a preferred embodiment, the apparatus uses a translucent element constituted by a ground glass plate comprising a reflecting metallised rear side. The plate is applied to the skin with its non-reflecting side; the greater the sebum secretion of the skin investigated, the more transparent the plate becomes. A monochromatic luminous flux is directed by a photodiode on to the ground surface of the plate and this luminous flux is received, after a first transition through the thickness of the plate, then a reflection on the metallised side, and finally, a second transition through the thickness of the plate, at the base of a phototransistor which supplies a voltage which is substantially proportional to the luminous flux received. A correlation exists between the quantity of sebum deposited on the plate and the voltage at the photransistor output. In this technique, the sebum quantity acts on the transmission of the luminous flux through the support used.

Applicants' assignees have found that a greater accuracy was obtained in the results of the detection of the quantity of the greasy product taken up on the skin or on the hair and deposited on a support, if instead of measuring the quantity of light transmitted through the support the quantity of light reflected on the support is measured. This mode of detection by reflection associated with the use of a matt support has the advantage of more dynamic measurements than those associated with the measurements by way of transmission or reflection on a shiny support.

SUMMARY OF THE INVENTION

Thus one aspect of the present invention provides a method for determining a quantity of a greasy product located on the surface of an element constituted by the skin or of the hair of a living subject, comprising applying a take-up strip to the element to be investigated, over a given time and with a given pressure, and evaluating the quantity of the greasy product deposited on the said strip optically, characterised in that a take-up strip is used whose side intended to come into contact with the element to be investigated is matt and has a specific reflection factor below 1%; the quantity of light reflected by the above mentioned side of the said strip being evaluated before and after impregnation with the greasy product, and the quantity of the greasy product located on the surface of the element investigated being derived therefrom.

When the reflected light is evaluated, the strip is situated on a non-reflecting support which absorbs the luminous radiation.

Advantageously, a take-up strip is chosen whose side intended to come into contact with the element to be investigated has a specular reflection factor below 1%, a surface condition whose smoothness is given by a value of the arithmetic rugosity Ra of less than 0.50 $\mu$m, microporosities whose absorption capacity of a fluid volume is less than 0.25 mm$^3$/cm$^2$, the depth of the diffusion being below 10 $\mu$m. This latter characteristic allows the greasy product to be rapidly balanced on the take-up strip.

In the above definition, the volume of the microporosities corresponds to the volume to liquid capable of being absorbed at the surface of the take-up strip and the Ra value is the mean rugosity calculated by the formula:

$$Ra = \frac{1}{L} \int_0^L |y|\, dx$$

where y is the height of a point of the surface in relation to the median plane taken as the reference value (such that $$\int_0^L y\, dx = o$$

and L is the length of the specimen.

A flexible or rigid strip may be used depending on the circumstances. When the sebum secretion of hair is investigated, a flexible take-up strip is used, making it possible to assume the curvature of the scalp; in the case of this use it is advantageous to use a rectangular 7 cm×1 cm take-up strip whose flexibility is such that it assumes at its centre a deflection of 10 to 15 mm under the loading of a weight of 200 g applied at its centre.

One may also use a translucent or opaque take-up strip. This take-up strip can be white, black or coloured.

The quantity of light reflected by the strip is preferably measured before and after impregnation with the greasy product, depending on the location of the said greasy product on this strip. In other words, the reflection reading along the whole strip produces a brightness curve depending on the location on the strip. This embodiment is particularly worthwhile when the sebum secretion of hair is investigated, the curve then reflecting the greasy aspect of the hair from its root up to its tip if the strip has been applied on the hair from the root to the tip.

It is, of course, possible in a simplified variant of the method in accordance with the invention to observe the strip with the naked eye after impregnation with the greasy product in order to draw qualitative conclusions regarding the greasy product content of the element to be investigated.

The presence of a greasy product on a coloured strip leads to a modification of the intensity of its colour (in the sense used by Munsell). One may advantageously choose a sufficiently dark colour, the eye being more sensitive to a variation in intensity when the colour is dark. In this connection, in the Munsell intensity scale wherein the intensity of black is equal to 1 and that of white equal to 9, the choice of a colour whose intensity is below 6 produces good results.

It is also worthwhile to use a magnetisable take-up strip which can be positioned in the optical investigation zone by a magnet; this technique affords easy detection of its brightness as will be described below. Such a magnetic fixing can, in particular, be used when the take-up strip is a section of a flexible magnetic tape.

Another aspect of the present invention provides a take-up strip having the above mentioned characteristics.

A further aspect provides an apparatus for the implementation of the above mentioned method. This apparatus is characterised in that it is constituted by:

a source of directional light producing a luminous beam intended to illuminate the take-up strip under an angle of incidence comprised between 10° and 70°;

a device for detecting the quantity of light reflected by the side of the take up strip intended to come into contact with the element to be investigated, before and after impregnation with the greasy product, this detection being, for instance, constituted by a phototransistor; and a device for the processing of the output signal supplied by the said detector.

In the case where a reading is obtained all along the strip to obtain a reflection curve which is an image of the distrubution of the greasy product over the surface investigated, the apparatus in accordance with the present invention comprises a support for the said strip, the said support being displaceable parallel to the plane of the latter.

Advantageously, the processing device for the output signal of the detector is constituted by an analog-digital converter associated with a programmable computer.

BRIEF DESCRIPTION OF THE DRAWINGS

To set out the advantages of the present invention more clearly, a comparative experiment will be described below between the modes of detection on (a) the light reflected by a take-up strip and (b) the light transmitted through the strip, and to render the invention more readily understood, an embodiment will be described with reference to the attached drawings by way of a purely illustrative and non-restrictive example.

In these drawings

FIG. 1 is a schematic view of an experimental device used for the comparison of the detection modes by transmission and by reflection;

FIGS. 2 and 3 each represent one of two possible electronic circuits used as a detector to measure the light received after transmission or reflection.

DESCRIPTION OF THE PREFERRED EMBODIMENT

Figure 4:
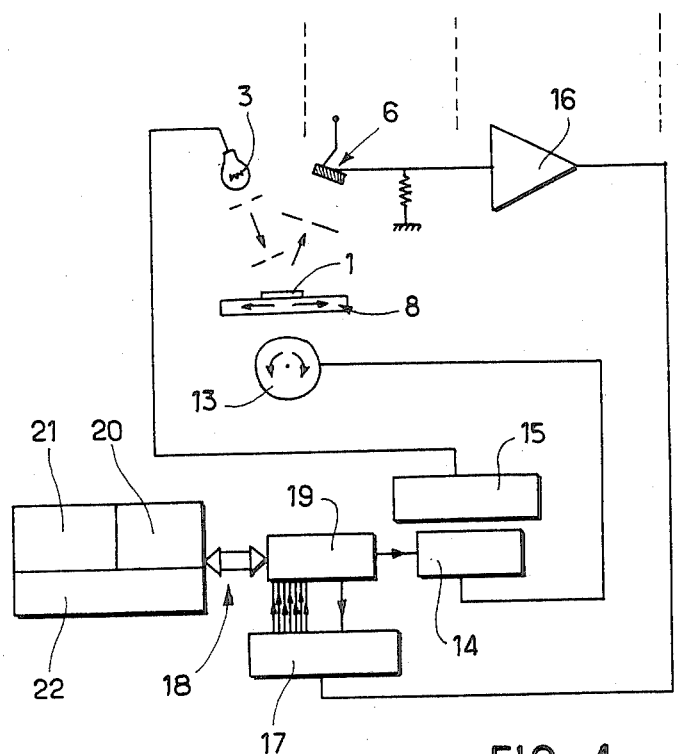
FIG. 4 is a schematic view of an apparatus for carrying out the invention.

In FIG. 1, there has been shown a transverse cross section of a strip 1 on whose upper side is a deposit of a greasy product 2. The side of the strip 1 whereon the product 2 can be deposited is matt. The strip 1 is illuminated by a light source 3 constituted by a "Midget" type of lamp supplied with a d.c. voltage. This lamp 3 provides a luminous beam inclined at an angle $\alpha = 30°$ in relation to the normal to the plane of the strip 1. At 4, is the location for a detector to detect the quantity of light reflected by the strip 1 along an axis of reflection symmetrical to the lighting axis with respect to the said normal, and 5 marks the location for a detector, along an axis which extends the lighting axis, of the quantity of light transmitted through the said strip 1.

To effect the above mentioned comparison, measurements have been obtained on two strips 1 made of relatively transparent material. The first is a strip of 1 mm thick ground glass and the second a section of adhesive tape sold under the trade name of "Scotch Magic" having a thickness of 0.07 mm.

In a first series of measurements, the same detection circuit has been used at 4 and 5, that is to say, the one represented in FIG. 2. The detector is constituted by a phototransistor 6 of the "ASEA 2B50 C" type whose collector is energised at 6 volts. The base of this phototransistor is illuminated by the reflected or transmitted luminous flux F. Between the earth and the emitter E, there is a 10 kΩ resistor 7. The measured signal $V_S$ is the potential difference across the terminals of the resistor 7. $V_S$ increases as the illumination of the phototransistor 7 increases.

In the case of each of the above mentioned strips, three reflection and transmission measurements $V_S$ have been effected each time before and after the sebum application; the values obtained with and without sebum respectively have been designated A and B. The sebum deposit is obtained by applying the strip to the forehead of a person for a given time and with a given pressure. The sensitivity is given by the ratio $(B-A)/A$.

The results are set out in Table I below. The comparison of the results in the two cases clearly shows that the signal transmitted by reflection appears as the one which is more sensitive to the presence of sebum on a take-up strip.

TABLE I

| SUPPORT | REFLECTION | | | TRANSMISSION | | |
|---|---|---|---|---|---|---|
| | without Sebum (A) | with Sebum (B) | Sensitivity (B-A)/A | without Sebum (A) | with Sebum (B) | Sensitivity (B-A)/A |
| Ground glass | 0,08 | 0,90 | 10,25 | 4,10 | 5,90 | 0,44 |
| | 0,09 | 0,70 | 6,8 | 4,70 | 5,96 | 0,27 |
| | 0,13 | 0,70 | 4,4 | 4,6 | 5,50 | 0,20 |
| Scotch Magic | 0,10 | 0,90 | 8 | 5,96 | 6,02 | 0,01 |
| | 0,15 | 0,60 | 3 | 5,95 | 6,00 | 0,008 |
| | 0,16 | 0,50 | 2,1 | 5,98 | 6,00 | 0,003 |

In a second series of measurements, applicants' assignees have tried to increase the sensitivity of the detector of the light transmitted through the strip without modifying the detector of the reflected light; for this purpose, the electronic detection circuit represented in FIG. 3 was only used at location 5. This circuit differs from the preceding one in that the emitter is directly connected to earth and in that a resistor 7 of the same rating as the preceding one is connected no longer to the emitter but to the collector. The voltage of the collector is still 6 volts. In this case, the signal $V_S$ is measured which is the difference in potential between the collector and earth. $V_S$ decreases as the irradiation increases.

The measurements and calculations carried out which are similar to the preceding ones are set out in Table II below.

TABLE II

| SUPPORT | REFLECTION | | | TRANSMISSION | | |
|---|---|---|---|---|---|---|
| | without Sebum (A) | with Sebum (B) | Sensitivity (B-A)/A | without Sebum (A) | with Sebum (B) | Sensitivity (B-A)/A |
| Ground glass | 0,09 | 0,98 | 9,9 | 2,70 | 1,00 | −0,63 |
| | 0,10 | 0,93 | 8,3 | 2,80 | 1,54 | −0,45 |
| | 0,15 | 0,95 | 5,3 | 2,70 | 1,20 | −0,56 |
| Scotch Magic | 0,05 | 0,25 | 4 | 1,2 | 0,22 | −0,82 |
| | 0,06 | 0,40 | 5,7 | 1 | 0,2 | −0,80 |
| | 0,09 | 0,50 | 4,6 | 1,8 | 0,20 | −0,89 |

Although a detector of higher sensitivity has been used for the detection by way of transmission through the strip, the sensitivity of the detection by transmission still remains well below that obtained with the detection by reflection.

The apparatus represented in FIG. 4 makes it possible to determine the quantity of light reflected by a strip carrying sebum in the zones wherein the sebum is located on this strip. This apparatus is particularly worthwhile where an analysis of sebum distribution along the hair between the root and the tip is required; a curve can be obtained representing the sebum distribution along the hair. To do this, a flexible rectangular strip 1 is applied to the hair, exerting constant pressure from the root towards the tip of the hair, the flexibility of the strip 1 allowing the latter to assume the contour of the skull. To form such a strip 1, a section of a magnetic tape, possibly mounted on a flexible plate may advantageously be chosen.

Figure 5:
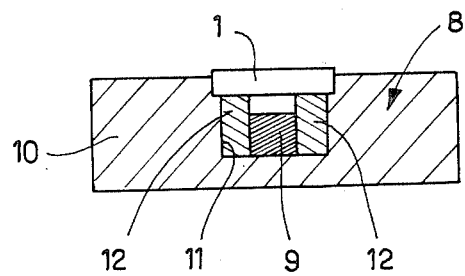
FIG. 5 shows a transverse cross-section of the positioning device of a take-up strip on a displaceable support of the apparatus of FIG. 4.

The appartus of FIG. 4 comprises a support 8 for the strip 1. FIG. 5 represents a cross-section of the said support. The support 8 is constituted by a displaceable sliding bed 10 having a channel-shaped groove 11; at the bottom of groove 11 is a magnet 9 between two ground bars 12 which contact the side of the strip 1 opposite to the one which has to carry the greasy product. Particles of iron oxide are applied to this strip 1 so that the strip 1 is subjected to the magnetic attraction of the magnet 9 and is thereby fixed flat on the support 8.

The surface of the support 8, or an intermediate surface, against or above which the strip 1 is placed, is non-reflecting and absorbing with regard to the luminous radiation used. Thus, an interference reflection of light which might have been able to pass through the strip 1 is avoided.

The displacement of the support 8 is achieved by means of a worm screw driven by a stepped motor 13 whose control unit is schematically outlined at 14.

The apparatus of FIG. 4 also comprises a lamp 3, such as described for the device of FIG. 1; this lamp is energised by the circuit 15; the apparatus comprises, moreover, a detection device constituted by a phototransistor 6 whose circuit layout is represented in FIG. 2 and has already been described.

It is known that the presence of sebum on the strip 1 modifies the reflection capacity, that is to say, the brightness of this strip; the phototransistor 6 provides a signal $V_S$ whose value is correlated to the quantity of sebum present on the strip 1, this signal $V_S$ being independent of the transverse sebum distribution on the strip. The signal $V_S$ coming from the phototransistor 6 is amplified by means of the amplifier 16, then it is digitalised in the analog digital converter 17, which transforms the signal whose amplitude is between 0 and 10 volts into a value read by a programmable computer 18 comprising a central unit with an interface 19, a printer 20, a monitor 21 and a keyboard 22. The functions of the computer 18 are: to instruct and control the displacement of the support 8 in relation to the reading head constituted by the lamp 3 and the detector 6, to store the data coming from the detector 6 in accordance with the position of the strip 1 in relation to the detector, and to process these data before editing a message containing various data concerning the sebum distribution along strip 1; these data comprise, in particular, graphics representing the distribution spectrum of the sebum along the strip, the surface value of the spectrum, the height of the peak, the width of the spectrum at mid-height, etc . . . . The curve representing the sebum distribution along the hair is derived from the difference between the spectrum obtained with the strip 1 carrying the sebum and the spectrum obtained with the strip 1 on its own before the sebum is applied.

It shall be duly understood that the embodiment described above is in no way restrictive and can give rise to any desirable modifications without thereby departing from the scope of the present invention.

We claim:

1. In a method for determining a quantity of a greasy substance on the surface of an element to be investigated, for example on the skin or the hair of a living subject, said method comprising the steps of:
   (a) applying a take-up strip to the element to be investigated so as to take up a quantity of the greasy substance, for a given time and with a given pressure:
   (b) and optically evaluating with light radiation the quantity of the greasy substance which has been deposited on the said strip; the improvement comprising:
   (c) using a take-up strip whose side intended to come into contact with the element to be investigated is matt and has a specular reflection factor below 1%, disposing the take-up strip on a support surface with said support surface being nonreflective and capable of absorbing the light radiation employed;
   (d) evaluating the light quantity reflected by the above mentioned side of the said strip before and after impregnation with the greasy substance; and
   (e) deriving the quantity of the greasy substance located on the surface of the element being investigated from the evaluated reflected qualities.

2. A method according to claim 1, comprising using a take-up strip whose side intended to come into contact with the element to be investigated has a surface condition having a smoothness corresponding to an arithmetic rigority (Ra) value below 0.50 μm.

3. A method according to claim 1, comprising using a take-up-strip whose side intended to come into contact with the element to be investigated has microporosities whose fluid absorption capacity is below 0.25 mm³/cm², the diffusion depth being less than 10 μm.

4. A method according to claim 1, comprising using a flexible take-up strip.

5. A method according to claim 1, comprising using a rigid take-up strip.

6. A method according to claim 1, comprising using a translucent take-up strip.

7. In a method for determining a quantity of a greasy substance on the surface of an element to be investigated, for example on the skin or the hair of a living subject, said method comprising the steps of:
   (a) applying a take-up strip to the element to be investigated so as to take up a quantity of the greasy substance, for a given time and with a given pressure:
   (b) and optically evaluating with light radiation the quantity of the greasy substance which has been deposited on the said strip; the improvement comprising:
   (c) using an opaque take-up strip whose side intended to come into contact with the element to be investigated is matt and has a specular reflection factor below 1%;
   (d) evaluating the light quantity reflected by the above mentioned side of the said strip before and after impregnation with the greasy substance; and
   (e) deriving the quantity of the greasy substance located on the surface of the element being investigated from the evaluated reflected qualities.

8. In a method for determining a quantity of a greasy substance on the surface of an element to be investigated, for example on the skin or the hair of a living subject, said method comprising the steps of:
   (a) applying a take-up strip to the element to be investigated so as to take up a quantity of the greasy substance, for a given time and with a given pressure:
   (b) and optically evaluating with light radiation the quantity of the greasy substance which has been deposited on the said strip; the improvement comprising:
   (c) using a colored take-up strip whose side intended to come into contact with the element to be investigated is matt and has a specular reflection factor below 1%;
   (d) evaluating the light quantity reflected by the above mentioned side of the said strip before and after impregnation with the greasy substance; and
   (e) deriving the quantity of the greasy substance located on the surface of the element being investigated from the evaluated reflected qualities.

9. In a method for determining a quantity of a greasy substance on the surface of an element to be investigated, for example on the skin or the hair of a living subject, said method comprising the steps of:
   (a) applying a take-up strip to the element to be investigated so as to take up a quantity of the greasy substance, for a given time and with a given pressure:
   (b) and optically evaluating with light radiation the quantity of the greasy substance which has been deposited on the said strip; the improvement comprising:
   (c) using a take-up strip having magnetic properties allowing said strip to be positioned and fixed by a magnet and whose side intended to come into contact with the element to be investigated is matt and has a specular reflection factor below 1%;
   (d) evaluating the light quantity reflected by the above mentioned side of the said strip before and after impregnation with the greasy substance; and
   (e) deriving the quantity of the greasy substance located on the surface of the element being investigated from the evaluated reflected qualities.

10. A method according to claim 1 wherein before and after impregnation with the greasy product, the quantity of the light reflected by the strip is measured according to the location on the take-up strip.

11. An apparatus for determining the quantity of a greasy substance on the surface of an element to be investigated, for example on the skin or the hair of a living subject, utilizing a take-up strip, comprising:
    (i) a directional light source producing a luminous beam intended to illuminate the take-up strip;
    (ii) detector means for detecting the quantity of light reflected by the side of the strip intended to come into contact with the skin, before and after impregnation with the greasy product; and
    (iii) means for processing the output signal of the said detector means;
    said apparatus further comprising support surface means for said take-up strip, said support surface means being nonreflective and capable of absorbing radiation from said directional light source.

12. An apparatus according to claim 11, comprising means mounting said support displaceably in a plane parallel to that of said take-up strip.

13. An apparatus according to claim 11, wherein the means for processing the output signal of the detector means comprises an analog-digital converter and a programmable computer associated therewith.

* * * * *